US00PP30510P3

(12) United States Plant Patent
Page

(10) Patent No.: US PP30,510 P3
(45) Date of Patent: May 21, 2019

(54) APPLE TREE NAMED 'RED BG'

(50) Latin Name: ***Malus domestica* Borkh.**
Varietal Denomination: Red BG

(71) Applicant: Page Family Nurseries Pty Ltd, Grove, Tasmania (AU)

(72) Inventor: Brian Page, Tasmania (AU)

(73) Assignee: Page Family Nurseries Pty LTD, Grove, Tasmania (AU)

( * ) Notice: Subject to any disclaimer, the term of this patent is extended or adjusted under 35 U.S.C. 154(b) by 0 days.

(21) Appl. No.: 15/732,164

(22) Filed: Sep. 26, 2017

(65) Prior Publication Data

US 2019/0098813 P1 Mar. 28, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875; A01H 5/02; A01H 5/08; A01H 5/0222; A01H 6/7418
See application file for complete search history.

*Primary Examiner* — June Hwu
(74) *Attorney, Agent, or Firm* — Michelle Bos Legal LLC

(57) ABSTRACT

'Red BG' is a limb sport mutation of 'Granny Smith'. The fruit of 'Red BG' exhibits a distinctive red overcolor, and is further distinguishable from 'Granny Smith' by its larger blossoms and darker stem.

3 Drawing Sheets

Latin name: *Malus domestica* Borkh.
Variety denomination: 'Red BG'.

BACKGROUND OF THE VARIETY

'Red BG' is a new and distinct variety of apple tree (*Malus domestica* Borkh), which variety originated as a limb sport mutation of 'Granny Smith' (not patented). 'Red BG' was discovered by the inventor in a cultivated orchard at Stanthorpe, Queensland, Australia in 2013, and was selected for further observation because of the distinctive red overcolor. 'Red BG' was first asexually propagated by budding in 2013 at Grove, Tasmania, Australia, and has since been observed to remain true to type over successive asexually propagated generations.

BRIEF DESCRIPTION OF THE VARIETY

The fruit of 'Red BG' exhibits a distinctive red overcolor as compared to the bright green color of 'Granny Smith', and is further distinguishable from 'Granny Smith' by its larger, pinker blossoms and darker stem, branches and shoots. 'Red BG' blooms two days earlier than 'Granny Smith'.

BRIEF DESCRIPTION OF THE PHOTOGRAPHS

Figure 1:
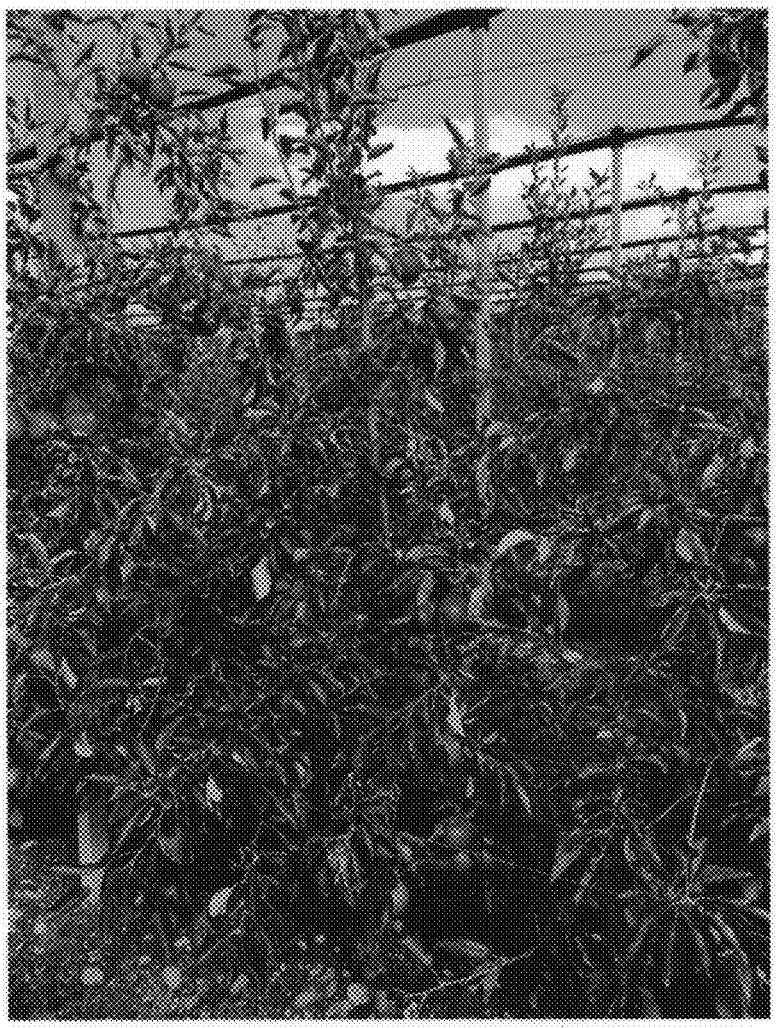
FIG. 1 shows a 'Red BG' apple tree and fruit near harvest time.
Figure 2:
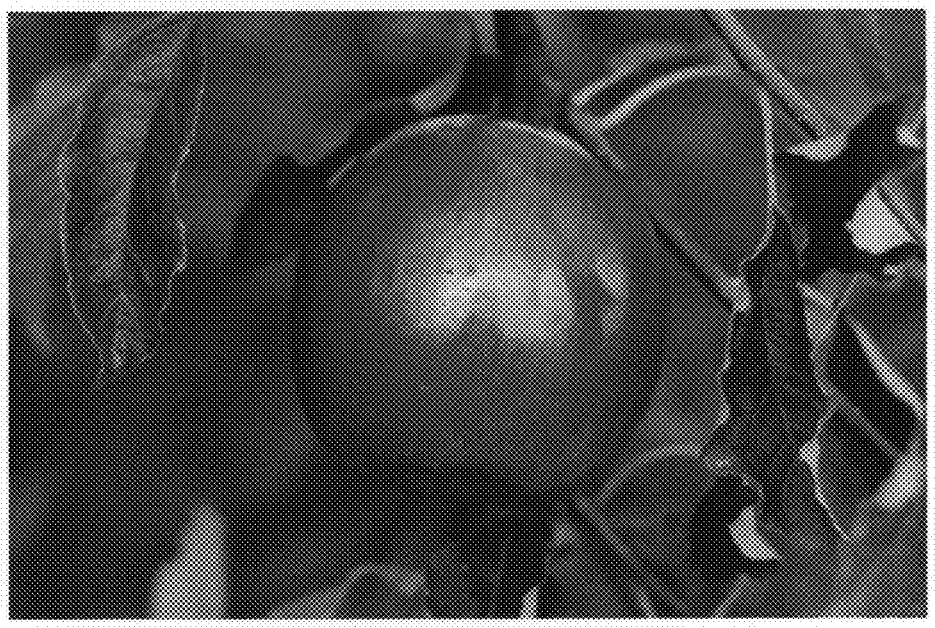
FIG. 2 shows leaves and fruit on a 'Red BG' apple tree.
Figure 3:
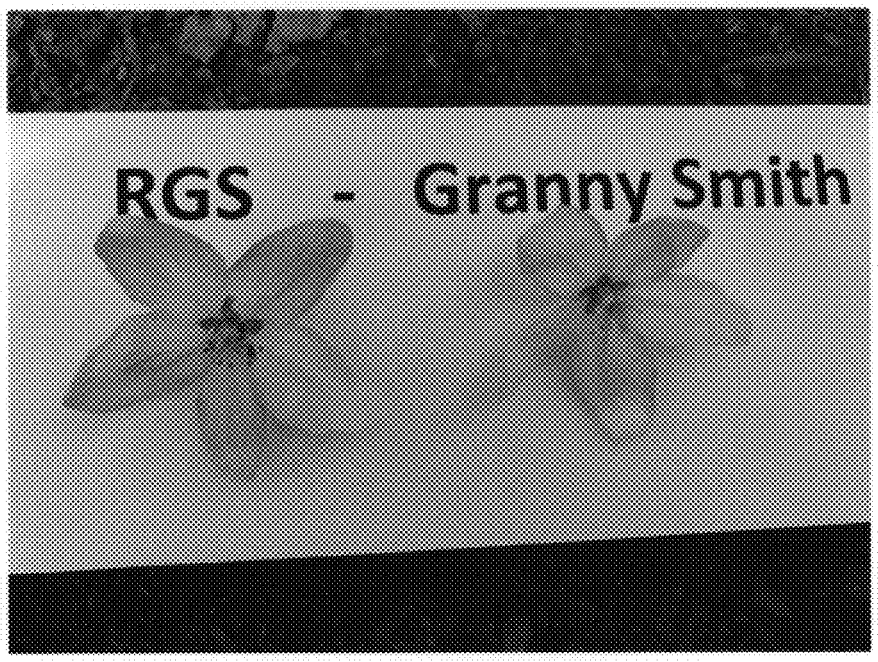
FIG. 3 shows flowers of 'Red BG' (labeled as "RGS") and 'Granny Smith'.

Actual colors will vary with lighting conditions; color characteristics of 'Red BG' apple tree should therefore be determined with reference to the observations described herein below, rather than from these illustrations alone.

DETAILED BOTANICAL DESCRIPTION OF THE VARIETY

The attached illustrations and the following detailed botanical description of 'Red BG' apple tree are based on observations made and photos taken during the 2017 growing season at Grove, Tasmania, Australia of trees planted in 2015 on M26 rootstock. All colors are described according to The Royal Horticultural Society Colour Chart (2001). The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Same as 'Granny Smith'.
*Type*.—Ramified.
*Habit*.—Drooping.
*Height*.—3 m, same as 'Granny Smith'.
*Trunk diameter* (*at* 30 *cm above the graft*).—28 mm+/−4 mm.
*Bark texture*.—Smooth.
*Bark color*.—Grey-brown N199A, darker than 'Granny Smith'.
*Type of bearing*.—On spurs and long shoots.

Branch (fruiting branches located at around 1 m above the graft union):

*Length*.—66 cm+/−23 cm.
*Diameter*.—1.1 cm+/−0.2 cm at 5 cm from the stem.
*Crotch angle*.—110 degrees+/−10 degrees.
*Bark color*.—Greyed-orange 164A.
*Lenticel length*.—0.10 cm+/−0.02 cm.

*Lenticel color*.—Greyed-white 156A.
*Number of lenticels per cm²*.—0 to 10 per cm².
One year old shoot:
*Length*.—20 cm to 70 cm.
*Color*.—Grey-brown N199A.
*Pubescence*.—Medium.
*Thickness*.—0.7 cm+/−0.1 cm.
*Internode length*.—2.7 cm+/−0.5 cm.
*Lenticel density*.—0 to 10 per cm².
Flower buds:
*Timing*.—2 days before 'Granny Smith'.
*Quantity per spur*.—6.
*Shape*.—Oval
*Length*.—0.6 cm.
*Diameter*.—0.4 cm.
*Color*.—Grey-brown N199A.
Flowers:
*Diameter of fully open flower*.—5.7 cm+/−0.5 cm.
*Relative position of petal margin*.—Not touching.
*Number per cluster*.—5 plus king flower.
*Date of first bloom*.—April 1 (2 days before 'Granny Smith').
*Date of full bloom*.—April 5 (2 days before 'Granny Smith').
*Pollination requirement*.—Pollenizer required (e.g., 'Gala').
*Unopened flower*.—Red-purple 60A.
Petals (all measured on king flower):
*Quantity per flower*.—5.
*Shape*.—Oval.
*Length*.—2.7 cm+/−0.1 cm.
*Width*.—1.9 cm+/−0.1 cm.
*Apex*.—Round.
*Base*.—Equilateral.
*Margin*.—Smooth.
*Color of upper surface*.—White N155B with red-purple N57D veins and edges.
*Color of lower surface*.—White N155B with red-purple N57D veins and edges.
Pistils:
*Position*.—Vessels of pistil are erect.
*Quantity*.—8 to 12 per flower.
*Size*.—Length 5.2 mm to 5.5 mm.
*Color*.—Yellow-green 145B.
Stigma:
*Position*.—Above anthers (like 'Golden Delicious').
*Size*.—0.09 cm+/−0.1 cm.
*Color*.—Yellow-green 145B with yellow 8C at edges.
Style:
*Size*.—0.8 cm+/−0.1 cm.
*Color*.—Yellow-green 145B.
Ovary:
*Size*.—0.5 cm+/−0.1 cm.
*Color*.—Yellow-green 145B.
Anthers:
*Quantity*.—10+/−2.
*Size*.—0.22 cm+/−0.2 cm.
*Color*.—Yellow 8C.
Pedicel:
*Length*.—1.6 cm+/−0.2 cm.
*Diameter*.—0.15 cm+/−0.03 cm.
*Color*.—Yellow-green 145B.
Sepals:
*Quantity*.—5.
*Color*.—Yellow-green 145B.
*Shape*.—Pointed, triangular.
*Margin*.—Smooth. 0.9 cm+/−0.1 cm.
Leaves:
*Shape*.—Oval.
*Length*.—81.5 mm+/−16 mm.
*Width*.—42.1 mm+/−12 mm.
*Length/width ratio*.—2 to 1.
*Blade margin*.—Serrate.
*Apex*.—Acute.
*Base shape*.—Aequilateral.
*Texture*.—Both surfaces glabrous; veins prominent on lower surface.
*Color of upper surface*.—Green 139A.
*Color of lower surface*.—Yellow-green 147C.
*Attitude in relation to shoot*.—Slightly upward.
Petiole:
*Length*.—39.5 mm+/−11.9 mm.
*Diameter*.—0.89 mm+/−0.39 mm.
*Color of upper surface*.—Green 138C.
*Color of lower surface*.—Green 138B.
Fruit:
*Quantity per cluster*.—1-2.
*Height*.—78 mm+/−7 mm.
*Diameter*.—78 mm+/−7 mm.
*Weight*.—238 grams+/−48 grams.
*Ratio of height to width*.—1 to 1.
*General shape in profile*.—Globose.
*Position of maximum diameter*.—50% in profile.
*Ribbing*.—Absent to Weak.
*Crowning at calyx end*.—Slight.
*Depth of eye basin*.—Medium, 9 mm+/−2 mm.
*Width of eye basin*.—23 mm+/−5 mm.
*Length of sepal*.—Short.
*Bloom of skin*.—Absent to Weak.
*Greasiness of skin*.—Absent to Weak.
*Background color of skin*.—Whitish green 149C.
*Amount of overcolor*.—Medium, up to about 70% of surface.
*Overcolor of skin*.—Red 46A.
*Intensity of overcolor*.—Light.
*Pattern of overcolor*.—Flush, striped and mottled.
*Amount of russet around stalk cavity*.—Absent to weak.
*Amount of russet on cheeks*.—Absent to weak.
*Area of russet around eye basin*.—Absent to weak.
*Length of stalk*.—Short, 14.6 mm+/−4.6 mm.
*Thickness of stalk*.—Very thin to thin, 1.5 mm+/−0.5 mm.
*Depth of stalk cavity*.—Medium, 12.4 mm+/−3.6 mm.
*Width of stalk cavity*.—Medium to Broad, 20 mm+/−2.5 mm.
*Firmness of flesh*.—Medium firm, 7.2 kg+/−1.3 kg.
*Flesh texture*.—Crisp.
*Aroma*.—Slightly Sweet.
*Juiciness*.—Medium to High.
*Brix*.—13 to 15.5 degrees.
*Flesh color*.—Greyed-green 192D.
*Number of lenticels*.—Absent to weak, 3+/−2 per cm².
*Size of lenticels*.—Very small.
*Aperture of locules*.—Open.
*Stem color*.—Greyed-orange 177D.
Seeds:
*Quantity per fruit*.—Up to 2 per chamber, maximum 8 per fruit.
*Shape*.—Acuminate.

*Length.*—7.5 mm+/−1.5 mm.
*Width.*—3.4 mm+/−0.6 mm.
*Color.*—Greyed-orange 177A.

Harvest:

*Time for harvest.*—Early April (in Australia).
*Number of picks.*—2 Picks; 20% on first pick.
*Amount of fruit produced per tree per harvest.*—15 kg; similar to 'Granny Smith', about 100 tons per hectare.
*Disease and pest resistance/susceptibility.*—Susceptible to bitter pit.
*Heat and cold tolerance.*—Believed to be similar to 'Granny Smith'.
*Market use.*—Fresh.
*Storage characteristics.*—Stores well, up to 12 months in ultra-low-oxygen controlled atmosphere storage; very good shelf life at room temperatures.

I claim:

1. A new and distinct apple tree, substantially as described and illustrated herein.

* * * * *